United States Patent [19]

Watson

[11] 4,248,860
[45] Feb. 3, 1981

[54] DENTIFRICES AND THEIR PREPARATION

[75] Inventor: Charles A. Watson, Ruislip, England

[73] Assignee: Lever Brothers Company, New York, N.Y.

[21] Appl. No.: 90,702

[22] Filed: Nov. 2, 1979

[30] Foreign Application Priority Data

Nov. 1, 1978 [GB] United Kingdom ............... 42771/78
Oct. 11, 1979 [GB] United Kingdom ............... 35265/79

[51] Int. Cl.$^3$ .............................................. A61K 7/16
[52] U.S. Cl. ........................................ 424/57; 424/49
[58] Field of Search .................................... 424/49-58; 51/309

[56] References Cited

U.S. PATENT DOCUMENTS

| | | | |
|---|---|---|---|
| 2,010,910 | 8/1935 | Atkins | 424/49 |
| 2,550,207 | 4/1951 | Tainter et al. | 424/49 |
| 2,818,371 | 12/1957 | Wessinger | 424/52 |
| 3,003,919 | 10/1961 | Broge | 424/49 |
| 3,060,098 | 10/1962 | Gershon | 424/52 |
| 3,662,060 | 5/1972 | Clippingdale et al. | 424/57 |
| 3,678,155 | 7/1972 | Clippingdale et al. | 424/52 |
| 3,981,988 | 9/1976 | Newman et al. | 424/49 |
| 4,034,076 | 7/1977 | Coulson et al. | 424/49 |
| 4,123,517 | 10/1978 | Baines et al. | 424/57 |
| 4,168,301 | 9/1979 | Pugh et al. | 424/49 |

*Primary Examiner*—Shep K. Rose
*Attorney, Agent, or Firm*—Michael J. Kelly; James J. Farrell; Melvin H. Kurtz

[57] ABSTRACT

A dentifrice comprising a dental abrasive and an orally-acceptable carrier therefor, wherein the dental abrasive comprises abrasive particles of alpha-alumina monohydrate (boehmite).

20 Claims, No Drawings

DENTIFRICES AND THEIR PREPARATION

This invention relates to dentifrices, and to an abrasive agent therefor.

Particles of inorganic abrasive material are widely incorporated into toothpaste formulations to aid in the removal of stains from the teeth. Such materials are sometimes referred to as polishing agents.

There are however a number of problems associated with use of the known abrasive agents, which include silica, chalk, dicalcium phosphate and alumina trihydrate.

In the first place, few of the known abrasive agents are compatible with cationic active compounds which it may be desired to include in dentifrice formulations, e.g. biguanido-group containing germicides such as chlorhexidine (hibitane). Silica, chalk, dicalcium phosphate, insoluble sodium metaphosphate and calcium pyrophosphate do not possess good compatibility with chlorhexidine.

In the second place, many known abrasive agents tend to adsorb and partially inactivate other components, e.g. flavourant components, commonly added to dentifrices, and it is desirable to minimise this effect.

In the third place, the hardness of an abrasive agent is not a variable, and it is desirable to have access to a number of abrasive agents of different hardness so as to allow choice of an abrasive agent of suitable hardness and abrasivity to complement other components of a dentifrice formulation. For example, it is known that chlorhexidine causes increase of stain uptake into dental pellicle and plaque, and use of a chlorhexidine-containing formulation accordingly brings undesired tooth staining when an abrasive agent of a known kind is included.

According to this invention, abrasive particles of alpha-alumina monohydrate (boehmite) are used as an abrasive agent in dentifrice formulations.

Boehmite is aluminium oxyhydroxide, otherwise alumina monohydrate, occurring in orthorhombic crystal form, and is distinguished from diaspore (another orthorhombic alumina monohydrate albeit of different form) by a Mohs hardness of 3½–4, solubility in caustic alkali solution at 125° C., and in its spectroscopic properties and pattern of thermal decomposition (see K. Wefers and G. M. Bell, "Oxides and Hydroxides of Aluminium", (1972) Alcoa Research Laboratories, Technical Paper No. 19).

It can be prepared by high-pressure hydrothermal alteration of alpha-alumina trihydrate. However, other preparative methods are available.

Boehmite is described in for example Royal Institute of Chemistry Lectures Monographs and Reports (1955) No. 3 "The Chemical Background of the Aluminium Industry" by T. G. Pearson (page 3). A grade of crystalline synthetic boehmite (density 3.01) is obtainable from BACO Chemicals (B.A. Chemicals Limited) under the Trade Mark Cera Hydrate.

Attention is drawn to a conflict of nomenclature: boehmite is termed alpha-alumina monohydrate in "Oxides and Hydroxides of Alumina" by K. Wefers and G. M. Bell, Aluminum Company of America, 1972 (Alcoa Technical Paper No. 19), while this term (alpha) is applied to the different material diaspore in Weiser and Mulligan, J.Phys.Chem. 38 1175-82 (1934). The modern (Alcoa) nomenclature is used in this specification.

It is explained that the invention relates to the use of particles of boehmite whether of natural or synthetic origin.

Boehmite is a somewhat harder abrasive agent (Mohs hardness 3½–4) than gibbsite (alumina trihydrate, Mohs hardness 2½–3). Surprisingly, however, it does not cause excessive or damaging dentine abrasion when formulated into a dentifrice.

We have found that use of boehmite in dentifrices, as abrasive agent, brings advantage.

It has unexpectedly been found that the use of boehmite can yield dentifrice compositions of appreciably thicker consistency than comparable compositions incorporating alpha-alumina trihydrate at similar or greater particle sizes and similar levels. This unexpected result in terms of thickening power allows the formulation of compositions of reduced mineral content and/or reduced contents of thickening organic gums, which are materials which can impart an unpleasant cloying feel to t adentifrice and are therefore advantageously used at levels as low as practicable.

Furthermore, it is also found unexpectedly that the flavourant in dentifrice compositions based on boehmite can give a stronger impression to the taste sense of the user than that of a comparative composition using alpha-alumina trihydrate at similar or greater particle size and concentration. It is thought that loss of flavourant can occur by surface adsorption onto the mineral abrasive agent of a dentifrice: it appears that this effect is less pronounced with boehmite than gibbsite. Stronger flavours or economy in flavourant can thus be achieved.

Furthermore, boehmite has greater abrasivity than gibbsite. This, combined with its compatibility with cationic germicides (e.g. hibitane), can enable minimisation of stain formation after the use of toothpastes containing such germicides, compared with otherwise similar formulations based on gibbsite.

The greater abrasivity than gibbsite also allows substitution of lower quantities of boehmite for gibbsite in otherwise equivalent dentifrice formulations with retention of cleaning power, or alternatively enhancement of toothcleaning power when substitution is made at equivalent levels.

Accordingly, by this invention we provide dentifrice compositions containing particles of boehmite as abrasive. The boehmite can be present either alone or in admixture with other abrasive agents, and the content of the boehmite may be chosen at any level according to convenience, for example at 5–60% by weight of the composition, e.g. 10–55%. Examples below illustrate the use of levels of 25% and 55%.

The average particle size of the boehmite can for example be within the range 8–20 microns ($\mu$), e.g. 7–12 microns, but any size suitable for dentifrice use, e.g. about 2–50, suitably 3–20, microns aps can be used. The material can be unmilled or milled, e.g. down to 5–6$\mu$, e.g. in the range 12–15$\mu$ aps. The boehmite particles can for example comprise aggregates of diameter up to about 50$\mu$ of sharp-edged crystallites of about 1–3$\mu$ across, or less, but the smaller particles may be individual crystals. Preparations consisting of particles that give colloidal dispersions are too fine and not recommended. Coarse, fibrillar, porous or colloidally dispersible particles make preparations that will usually not give a satisfactory paste. Such unsuitable materials might have specific surface areas of a very high order, e.g. 300 m$^2$/g consistent with microcrystalline or porous particle structure. Suitable preparations have much lower specific surface areas, e.g. 5 m$^2$/g or below, down to 0.5 m$^2$/g. The highly satisfactory commercial example of boehmite, Cera Hydrate (Trade Mark), has an average particle size by Coulter Counter (Trade Mark) in the range 12–26μ, believed mostly in the range 12–16μ. All or substantially all, i.e. 92–95%, of the material passes a 300 BS Sieve in a wet sieving test. The specific surface area is less than 5 m$^2$/g, e.g. 0.5–3 m$^2$/g.

It will be appreciated that any of a number of dentifrice formulations containing boehmite can be formulated in accordance with the invention, and that the details of the formulations can be chosen by methods known in the art to meet any given criterion, such as stability during a desired period, or lack of corrosivity.

It has been found for example that the use of boehmite in dentifrices, as in the case of other abrasive agents based on alumina, can be accompanied by corrosion of unlacquered dentifrice tubes in which the dentifrice formulations are packed, unless measures are taken. Such measures are, for example, to include orthophosphate in boehmite-containing dentifrice formulations. The use of orthophosphate in dentifrices based on alpha-alumina trihydrate is described for example in UK Specification Nos. 1,277,585 and 1,277,586. The phenomenon of corrosion and its prevention in the case of compositions based on alpha-alumina trihydrate is well described in the prior art. The present invention includes formulations based on the application and adaptation of known corrosion-preventive measures to the dentifrices based on boehmite, and the use of lacquered tubes for untreated formulations in the alternative.

Dentifrice formulations according to the invention can include the boehmite abrasive together with a stabilising amount of orthophosphate at a level of, for example, at least 0.4% to 0.5%, e.g. 1% to 1.5%.

The invention is further illustrated by means of the following Examples.

EXAMPLE 1

One preferred application of boehmite as an abrasive is in a toothpaste containing a cationic germicide, which tends to encourage staining. Here, the increased cleaning powder of the harder than normal abrasive is utilised for example at 55% level as a counter to the stain-encouraging tendency of the cationic germicide.

A suitable dentifrice formulation by way of example only is as follows:

| | |
|---|---|
| Boehmite | 55% |
| Glycerine | 27% |
| Hydroxyethyl cellulose | 1.1% |
| Chlorhexidine gluconate | 0.8% |
| Titanium dioxide | 0.5% |
| Flavour | 1% |
| Water | 14.6% |

This formulation is notably thick and the amount of hydroxyethyl cellulose binder can be reduced if desired to as little as about 0.7%. In a comparative toothpaste using gibbsite an acceptable paste thickness could not be obtained with as little binder as 0.7%.

In general, boehmite-containing formulations can be made up using less binder than would be required to achieve a formulation of equivalent thickness and cohesion using conventional abrasives.

EXAMPLE 2

A second preferred application of boehmite is in a composition containing a lower level of abrasive, e.g. 25% boehmite.

A suitable formulation by way of example is as follows:

| | |
|---|---|
| Boehmite | 25% |
| Precipitated silica | 5% |
| Sorbitol syrup | 35% |
| Sodium lauryl sulphate | 1.5% |
| Xanthan gum | 1.2% |
| Monosodium phosphate | 0.15% |
| Sodium monofluorophosphate | 0.8% |
| Saccharin | 0.15% |
| Flavour | 0.9% |
| Titanium dioxide (Trade Mark: Laporte Tiona WD) | 0.5% |
| Water | to 100% |

In this formulation, the low level of relatively harder boehmite particles allows economy in the inclusion of flavourant, owing, it is thought, to lower adsorption of flavourant onto the abrasive. At the same time this example formulation has a noticeably fresher flavour than conventional pastes based on alumina trihydrate.

EXAMPLES 3 AND 4

Further boehmite-containing toothpaste compositions were formulated as follows:

| | Example 3 | Example 4 |
|---|---|---|
| Boehmite (Cera Hydrate ex Baco Chemicals Limited) | 30% | 30% |
| Sorbitol syrup (70%) | 35% | 35% |
| Sodium lauryl sulphate | 1.5% | 1.5% |
| Sodium carboxymethylcellulose | 1.4% | 1.4% |
| Precipitated silica | 4% | 4% |
| Benzoic acid | 0.14% | — |
| Saccharin | 0.2% | 0.2% |
| Flavour | 1% | 1% |
| Formaldehyde | 0.04% | 0.04% |
| Titanium dioxide (ex Laporte, Tiona G) | 1% | 1% /... |
| Disodium orthophosphate (anhydrous) | 0.5% | 0.15% |
| Monosodium orthophosphate (dihydrate) | 0.5% | — |
| Orthophosphoric acid | — | 0.05% |
| Water | to 100% | to 100% |

These formulations gave good cleaning power, had notably fresh flavour, and did not gas on storage trials lasting for some months.

EXAMPLE 5

A further dentifrice was formulated in which boehmite particles were used in admixture with other abrasive particles, in this case of gibbsite.

| | |
|---|---|
| Boehmite (ex Baco Chemicals Limited, grade CH2) | 30% |
| Gibbsite (grade AF 239) | 25% |
| Glycerol | 27% |
| Hydroxyethyl cellulose | 0.8% |
| Flavour | 1% |
| Titanium dioxide (ex Laporte, Tiona G) | 0.5% |
| Water | to 100% |

This dentifrice showed good cleaning power and a very fresh flavour. It was not necessary to use another alumina abrasive with the boehmite: other abrasives such as dicalcium phosphate (anhydrous or dihydrate), precipitated chalk, insoluble sodium metaphosphate, silica xerogel, or or mixtures thereof, were also suitable.

It has been noticed that a number of dentifrice formulations based wholly or partly on boehmite as an abrasive impart a notably conspicuous lustre to teeth cleaned with them.

I claim:

1. In a dentifrice composition comprising a dental abrasive and an orally-acceptable carrier therefor, the improvement wherein the dental abrasive comprises abrasive particles of alpha-alumina monohydrate (boehmite).

2. A dentifrice according to claim 1, wherein the average particle size of the boehmite particles is in the range 2–5μ.

3. A dentifrice according to claim 2, wherein the average particle size of the boehmite particles is in the range 3–20μ.

4. A dentifrice according to claim 1, wherein the average particle size of the boehmite particles is at least 7μ and all or substantially all of the material passes a 300 BS Sieve in a wet sieving test.

5. A dentifrice according to claim 1, wherein the boehmite particles include aggregates of shap-edged crystallites.

6. A dentifrice according to claim 1, comprising 5–60% by weight of the boehmite particles.

7. A dentifrice according to claim 1, comprising boehmite as sole abrasive agent.

8. A dentifrice according to claim 7, comprising at least 25% boehmite.

9. A dentifrice according to claim 8, further comprising orthophosphate to stabilise the composition against gassing.

10. A dentifrice according to claim 9, comprising at least 0.4% orthophosphate.

11. A dentifrice according to claim 10, comprising at least 0.8% orthophosphate.

12. A dentifrice according to claim 11, comprising 1% to 1.5% orthophosphate.

13. A dentifrice according to claim 7, further comprising a cationic germicide.

14. A dentifrice according to claim 1, comprising boehmite in admixture with another abrasive.

15. A dentifrice according to claim 14, wherein the other abrasive comprises gibbsite, dicalcium phosphate (anhydrous or dihydrate), precipitated chalk, insoluble sodium metaphosphate, silica xerogel, or mixtures thereof.

16. A dentifrice according to claim 14 or 15, with boehmite up to 30% by weight.

17. A dentifrice according to claim 14 or 15, with boehmite up to 25% by weight.

18. A dentifrice according to claim 14 or 15, with orthophosphate to stabilise against gassing.

19. In a process of preparing a dentifrice composition by incorporating a dental abrasive with an orally-acceptable carrier therefor, the improvement which comprises incorporating abrasive particles of alpha-alumina monohydrate (boehmite).

20. A process according to claim 19, wherein said abrasive particles include aggregates of sharp-edged crystallites substantially consisting of boehmite and said particles also include boehmite particles of average particle size at least 7μ and able to pass a 300 BS Sieve in a wet sieving test.

* * * * *

UNITED STATES PATENT AND TRADEMARK OFFICE
CERTIFICATE OF CORRECTION

PATENT NO. : 4,248,860
DATED : February 3, 1981
INVENTOR(S) : Charles Andrew Watson It is certified that error appears in the above-identified patent and that said Letters Patent are hereby corrected as shown below:

Column 2, line 19: change "2-5µ" to -- range 2-50µ --

Column 5, line 29: change "shap-edged" to -- sharp-edged --

Column 6, line 2: change "stabilise" to -- stabilize --

Column 6, line 24: change "stabilise" to -- stabilize --

Signed and Sealed this

Seventeenth Day of November 1981

[SEAL]

Attest:

GERALD J. MOSSINGHOFF

Attesting Officer   Commissioner of Patents and Trademarks